United States Patent [19]

Archibald

[11] Patent Number: 5,154,704
[45] Date of Patent: Oct. 13, 1992

[54] IV CLAMP WITH TUBE CLIP

[76] Inventor: G. Kent Archibald, 111 E. Kellogg Blvd., Suite 3006, St. Paul, Minn. 55101

[21] Appl. No.: 607,299

[22] Filed: Oct. 31, 1990

[51] Int. Cl.⁵ .............................................. A61M 5/00
[52] U.S. Cl. .................................... 604/250; 604/65; 251/4; 251/9
[58] Field of Search .................. 604/65, 67, 246, 250, 604/253; 128/DIG. 13; 251/4, 6, 7, 9

[56] References Cited

U.S. PATENT DOCUMENTS

| | | |
|---|---|---|
| Re. 32,294 | 11/1986 | Knute . |
| 2,761,445 | 9/1956 | Cherkin . |
| 2,807,012 | 9/1957 | Schwarz . |
| 2,842,331 | 7/1958 | Anderson ............................... 251/6 |
| 3,163,176 | 12/1964 | Darling ................................. 604/65 |
| 3,197,068 | 7/1965 | Corbin et al. . |
| 3,217,709 | 11/1965 | Schneider et al. . |
| 3,252,623 | 5/1966 | Corbin et al. . |
| 3,384,080 | 5/1968 | Muller . |
| 3,390,577 | 7/1968 | Phelps et al. . |
| 3,449,952 | 6/1969 | Brown et al. . |
| 3,450,153 | 6/1969 | Hildebrandt et al. . |
| 3,500,366 | 3/1970 | Chesney et al. . |
| 3,545,271 | 12/1970 | Amir et al. . |
| 3,563,090 | 2/1971 | Deltour . |
| 3,593,579 | 7/1971 | Hindman et al. . |
| 3,596,515 | 8/1971 | Cramer . |
| 3,601,124 | 8/1971 | Petree . |
| 3,623,474 | 11/1971 | Hellman et al. . |
| 3,641,543 | 2/1972 | Rigby . |
| 3,647,117 | 3/1972 | Hargest . |
| 3,655,095 | 4/1972 | Kienitz . |
| 3,670,926 | 6/1972 | Hill . |
| 3,739,777 | 6/1973 | Gregg . |
| 3,832,998 | 9/1974 | Gregg . |
| 3,871,229 | 3/1975 | Fletcher . |
| 3,890,968 | 6/1975 | Pierce et al. . |
| 3,985,133 | 10/1976 | Jenkins et al. . |
| 3,990,443 | 11/1976 | Fletcher . |
| 4,038,981 | 8/1977 | LeFevre et al. . |
| 4,105,028 | 8/1978 | Sadlier et al. . |
| 4,111,198 | 9/1978 | Marx et al. . |
| 4,137,940 | 2/1979 | Faisandier . |
| 4,261,388 | 4/1981 | Shelton . |
| 4,314,484 | 2/1982 | Bowman . |
| 4,346,606 | 8/1982 | Cannon et al. . |
| 4,397,642 | 8/1983 | Lamadrid . |
| 4,432,761 | 2/1984 | Dawe . |
| 4,432,762 | 2/1984 | Dawe . |
| 4,447,232 | 5/1984 | Sealfon et al. . |
| 4,496,351 | 1/1985 | Hillel et al. . |
| 4,498,901 | 2/1985 | Finch . |
| 4,504,263 | 5/1985 | Steuer et al. . |
| 4,509,943 | 4/1985 | Hanzawa . |
| 4,533,350 | 8/1985 | Danby et al. . |
| 4,557,728 | 12/1985 | Sealfon et al. . |
| 4,583,975 | 4/1986 | Pekkarinen et al. . |

(List continued on next page.)

FOREIGN PATENT DOCUMENTS 1541363  4/1969  Fed. Rep. of Germany ...... 604/250

Primary Examiner—John D. Yasko
Assistant Examiner—Anthony Gutowski
Attorney, Agent, or Firm—Kinney & Lange

[57] ABSTRACT

An apparatus clamps an intravenous (IV) tube used in an infusion device to control flow rate of IV fluid in the IV tube. A tube clip has first and second pinching members biased for exerting a pinching force on the IV tube. The first and second pinching members are positionable for insertion of the IV tube between them. A pair of clamping members are coupled to a clamp housing and are positionable for insertion of a portion of the tube clip between the pair of clamping members. The pair of clamping members operably engage the tube clip to variably offset the pinching force based on relative position of the pair of clamping members with respect to one another. A manual adjustment mechanism is coupled to at least one of the pair of clamping members and is used to manually adjust the relative position of the pair of clamping members relative to one another to set a desired flow rate in the IV tube.

17 Claims, 4 Drawing Sheets

U.S. PATENT DOCUMENTS

| | | |
|---|---|---|
| 4,585,441 | 4/1986 | Archibald . |
| 4,613,325 | 9/1986 | Abrams . |
| 4,623,331 | 11/1986 | Cewers et al. . |
| 4,634,426 | 1/1987 | Kamen . |
| 4,645,489 | 2/1987 | Krumme et al. . |
| 4,668,216 | 5/1987 | Martin et al. . |
| 4,673,820 | 6/1987 | Kamen . |
| 4,680,977 | 7/1987 | Conero et al. . |
| 4,681,563 | 7/1987 | Deckert et al. . |
| 4,681,569 | 7/1987 | Coble et al. . |
| 4,714,463 | 12/1987 | Archibald et al. . |
| 4,741,736 | 5/1988 | Brown . |
| 4,775,368 | 10/1988 | Iwatschenko . |
| 4,821,028 | 4/1989 | Deckert et al. . |
| 4,909,786 | 3/1990 | Gijselhart et al. ............... 604/253 |
| 5,017,192 | 5/1991 | Dodge et al. ...................... 604/250 |

1

IV CLAMP WITH TUBE CLIP

INCORPORATION BY REFERENCE

The following patent applications are hereby fully incorporated by reference: a patent application entitled SPRING POWERED FLOW RATE IV CONTROLLER, Ser. No. 07/458,286, filed on Dec. 28, 1989, by G. Kent Archibald; and, a patent application entitled AUTOMATIC IV CLAMP, Ser. No. 07/486,158, filed on Feb. 28, 1990, by G. Kent Archibald.

CROSS REFERENCE TO CO-PENDING PATENT APPLICATIONS

The following patent applications have been filed on even date herewith and have the same inventor as the present patent application: DROP DETECTOR, Ser. No. 07/606,134 and IV CLAMP WITH MANUAL ADJUSTMENT, Ser. No. 07/606,093.

BACKGROUND OF THE INVENTION

The present invention relates to an intravenous (IV) infusion device. More particularly, the present invention relates to an automatic clamp for controlling flow rate of IV fluid in an infusion device.

Infusion devices are used to deliver IV fluids to patients. A typical infusion device includes a fluid source or reservoir, a drip chamber and an IV tube set. Fluid drips from the reservoir through the drip chamber into the IV tube. The rate at which the fluid drips from the fluid reservoir is proportional to the flow rate of the fluid through the IV tube.

Physicians often require IV fluid to be delivered to patients at a certain rate. Therefore, it is necessary to control the flow rate of the IV fluid through the IV tube.

In the past, flow rate controllers were developed which used electromechanical devices to apply a pinching force to the IV tube. By pinching the IV tube, the flow of IV fluid through the IV tube was restricted and the flow rate was controlled. The degree of flow restriction varied based on a feedback system.

However, typical IV tubes are formed of a material having a certain resilience. Most of the pinching force required to restrict flow of IV fluid through the IV tube is needed to overcome the resilience of the IV tube. Therefore, an IV controller requires a large amount of electrical energy to drive the electromechanical pinching device. This is especially true where the pinching device is used with a standard set of IV tubes because of the stiffness of the IV tubes. For an IV controller of this type to be provided with an adequate amount of electrical energy, it must either by connected to an AC source or have a large battery. In either case, this type of IV device is not a practical device to be used with ambulatory patients.

For these reasons, there have been several attempts to provide the medical community with an IV control device that is small and that contains its own power source. One example is the Danby U.S. Pat. No. 4,533,350 which utilizes a battery for control power. In order to keep the power requirements of the controller low, a special IV tube set having a special control valve is used. The special IV tube set is designed to decrease the amount of pinching force required to restrict flow in the IV tube in order to achieve a corresponding decrease in the power requirements of the controller.

Similarly, the Krumme U.S. Pat. No. 4,645,489 illustrates an attempt to provide a small IV control device with self-contained energy requirements. The device in Krumme uses a shaped memory alloy driven by electrical energy to provide the pinching force. However, as with Danby, the Krumme patent requires a special IV tube set to reduce the required pinching force.

Because of the special IV tube sets required in both the Danby and Krumme patents, the cost of the IV device is higher than it would be if a standard IV tube set were used. Additionally, this extra cost is recurring each time the device is used since a new IV tube set is required for each infusion.

Another technique for controlling the flow of fluid in an IV tube involves a simple mechanical clamp. The flow rate through the IV tube is initially set by an attending medical person observing the drip rate in the drip chamber. The clamp is adjusted to maintain a set flow rate. Periodically, the attending medical person returns to the IV set, monitors the flow rate and adjusts the mechanical clamp. There is no automatic feedback system for variably controlling the clamp to adjust the flow rate to compensate for deviations caused by varying environmental conditions such as hydrostatic pressure or venous pressure. Hence, the technique is inefficient because of the time required by the attending medical person to periodically monitor and adjust the mechanical clamp. In addition, this technique requires the attending medical person to make an accurate determination of the flow rate each time the mechanical clamp is adjusted. Therefore, errors are likely.

Spring power has been used in the past to propel the IV fluid from the reservoir. For example, the Brown U.S. Pat. No. 4,741,736 teaches a programmable infusion pump which has a constant force spring to force the fluid from the reservoir. However, flow restriction is controlled by a mechanical screw clamp which is not automatically variable.

Other spring power propulsion devices are taught by the Muller U.S. Pat. No. 3,384,080; the Hargest U.S. Pat. No. 3,647,117; the Hill U.S. Pat. No. 3,670,926 and the Sealfon U.S. Pat. No. 4,447,232. All of these devices teach the use of spring driven pumps to force the IV fluid from the reservoir.

Another major power requirement for past electromechanical IV clamps, in addition to overcoming the tube resilience in flow rate control, is the requirement of setting an initial flow rate. In past electromechanical flow rate controllers, an operator would insert the IV tube into the flow rate controller and enter a desired initial flow rate through, for example, a keypad entry system. Then, the electromechanical flow rate controller would drive a pinching device until the initial flow rate was achieved. This would sometimes require electromechanically driving the pinching device a relatively large distance, thus resulting in a large amount of power consumption during this phase of operation.

SUMMARY OF THE INVENTION

The present invention provides an IV clamp with low power requirements. Therefore, the controller is compact and can be supplied with power by a small source.

An apparatus clamps an intravenous (IV) tube used in an infusion device to control flow rate of IV fluid in the IV tube. A tube clip has first and second pinching members biased for exerting a pinching force on the IV tube. The first and second pinching members are positionable for insertion of the IV tube between them. A pair of clamping members are coupled to a clamp housing and are positionable for insertion of a portion of the tube clip between the pair of clamping members. The pair of clamping members operably engage the tube clip to variably offset the pinching force based on relative position of the pair of clamping members with respect to one another. A manual adjustment mechanism is coupled to at least one of the pair of clamping members and is used to manually adjust the relative position of the pair of clamping members relative to one another to set a desired flow rate in the IV tube.

DETAILED DESCRIPTION OF THE PREFERRED EMBODIMENTS

Figure 1:
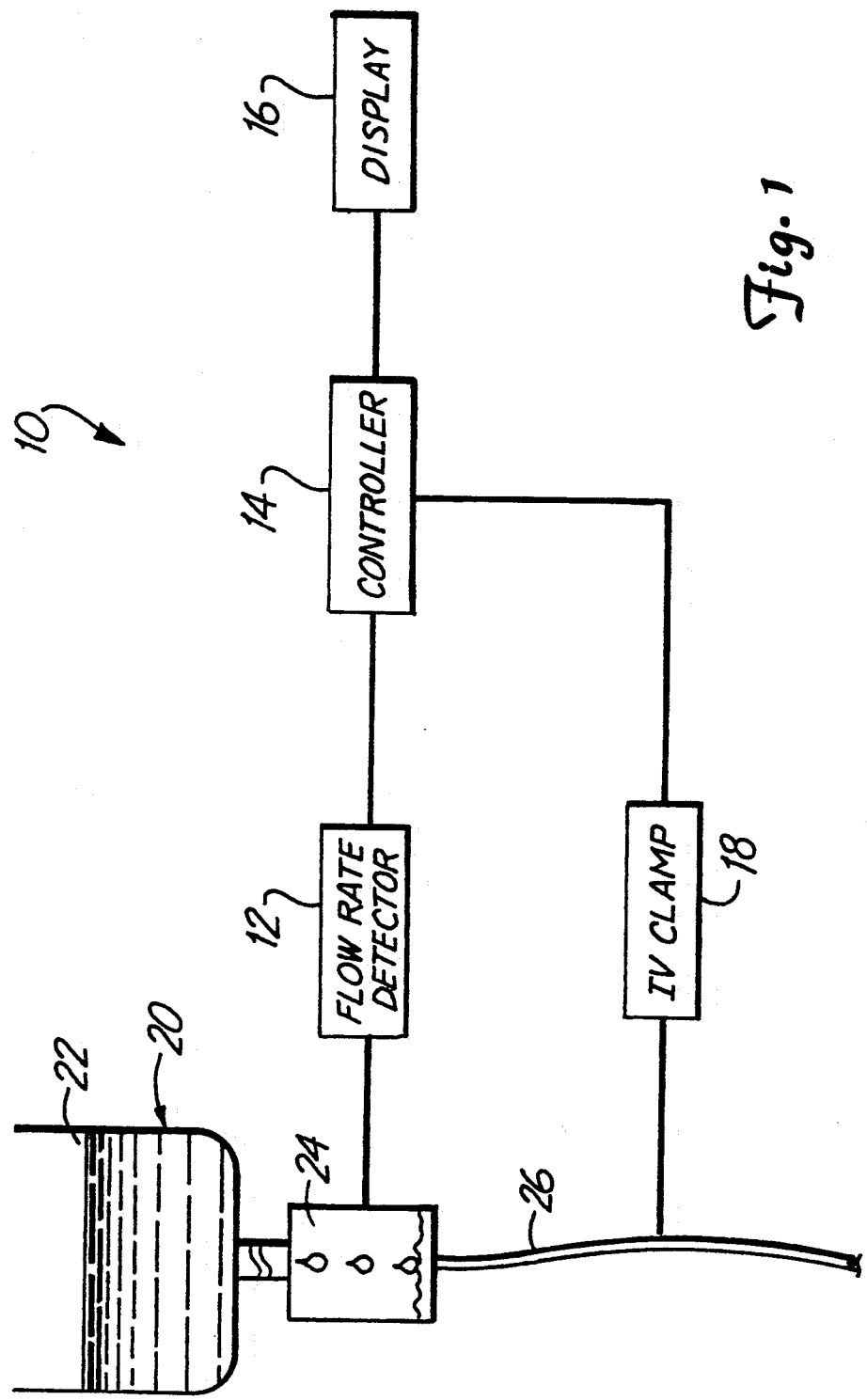
FIG. 1 is a block diagram showing an infusion system using an IV clamp according to the present invention.

FIG. 1 is a block diagram of infusion system 10 which includes flow rate detector 12, controller 14, display 16, IV clamp 18 and infusion device 20. Infusion device 20 includes fluid reservoir 22, drip chamber 24 and IV tube 26.

In order to set an initial flow rate, an operator adjusts IV clamp 18 to pinch IV tube 26, and thereby restrict flow of IV fluid through IV tube 26 until a desired flow rate is achieved. Flow rate detector 12 can be any type of suitable flow rate detector. In this preferred embodiment, flow rate detector 12 is an optical drop detector which provides a drop signal to controller 14 representing the flow rate of IV fluid through IV tube 26. Controller 14 provides display 16 with a display signal representative of the flow rate detected by flow rate detector 12. Display 16, in turn, displays the flow rate. In this preferred embodiment, display 16 is an LCD display. Based on the flow rate detected by flow rate detector 12, and the initial flow rate set by the operator, controller 14 controls IV clamp 18 to variably restrict the flow of IV fluid through IV tube 26.

Figure 2:
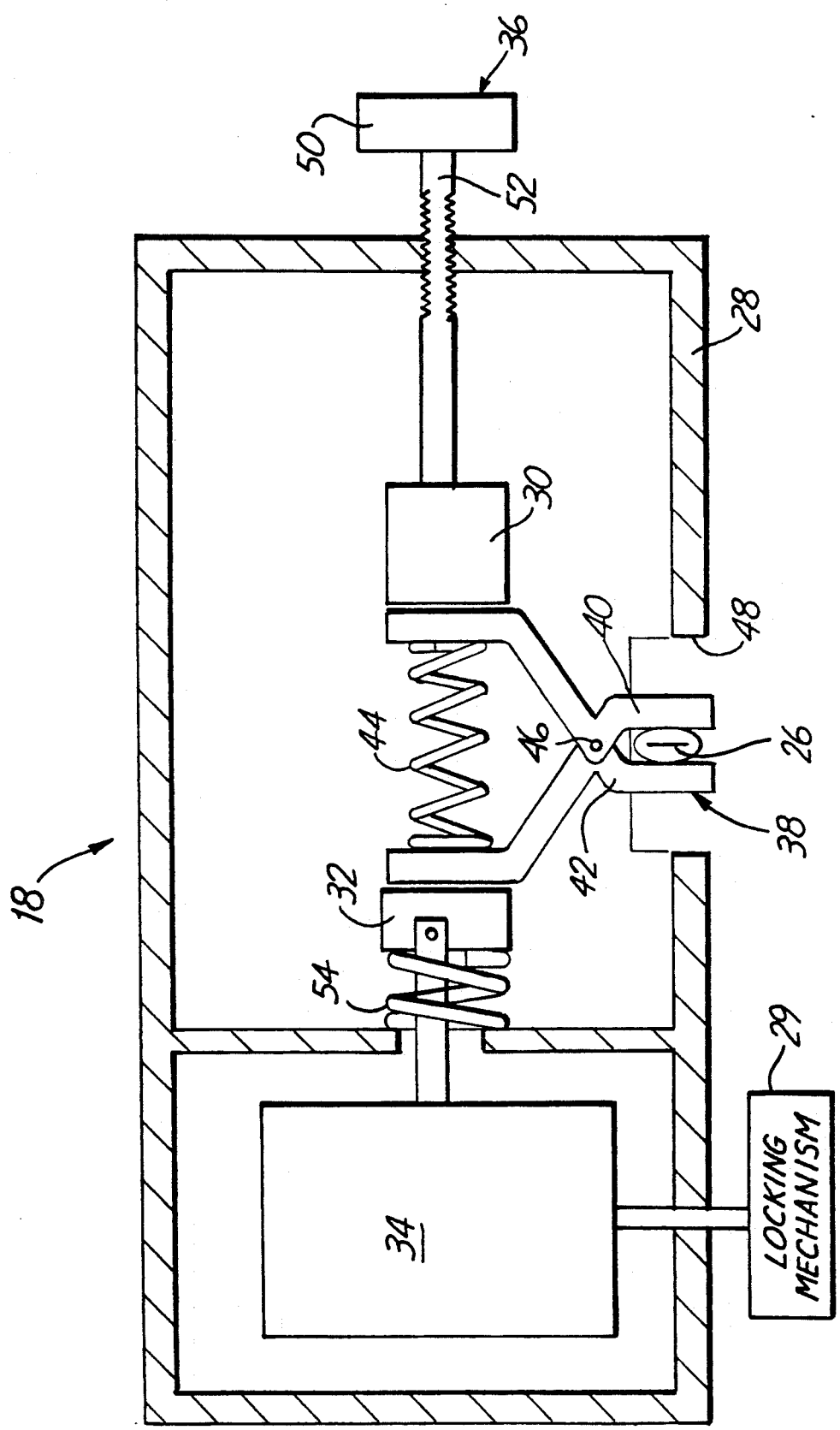
FIG. 2 is a more detailed diagram of an IV clamp of the present invention shown in partial cross section.

FIG. 2 shows a more detailed diagram of IV clamp 18. IV clamp 18 includes housing 28, clamping members 30 and 32, motor 34, manual adjustment mechanism 36 and removable tube clip 38. Tube clip 38 includes first pinching member 40, second pinching member 42 and spring 44. Pinching members 40 and 42 are pivotally coupled at pivot point 46 and are biased in a pinching position by spring 44 to pinch an IV tube 26 inserted between them.

In operation, IV tube 26 is inserted between pinching members 40 and 42 of tube clip 38. In this preferred embodiment, the spring force of spring 44 is strong enough to completely close off IV tube 26, thereby stopping flow of IV fluid through IV tube 26. Then, removable tube clip 38 is inserted within housing 28 through gap 48 and positioned between clamping members 30 and 32.

An operator then sets a desired flow rate by manipulating manual adjustment mechanism 36. Manual adjustment mechanism 36 includes knob 50 which is connected to clamping member 30 and housing 28 by threaded shaft 52. By rotating knob 50, the operator moves clamping member 30 either in the direction toward or away from motor 34. By moving clamping member 30 in the direction toward motor 34, clamping member 30 begins to exert a compressive force on springs 44 and 54. Motor 34 is slidably coupled within housing 28 by locking mechanism 29 during the manual adjustment of the desired flow rate such that clamping member 32 is movable within housing 28 in response to the compression force exerted by clamping member 30.

When the compression force exerted by clamping member 30 starts to overcome the spring forces of springs 44 and 54, pinching members 40 and 42 of tube clip 38 begin to open in a scissor-like manner. Thus, IV tube 26 begins to open and IV fluid begins to flow through IV tube 26.

Once a desired flow rate of IV fluid through IV tube 26 is reached, the operator indicates to controller 14 that the desired flow rate has been set and the operator also locks motor 34 in place relative to housing 28. The operator can indicate to controller 14 that the desired flow rate is set in any number of ways including the probe and sensor method described in the Archibald U.S. patent application Ser. No. 07/486,158 filed Feb. 28, 1990 entitled AUTOMATIC IV CLAMP. That patent application is fully incorporated herein by reference. Further, motor 34 can be locked in place relative to housing 28 in any number of ways, including the locking assembly described in the abovementioned patent application incorporated herein by reference.

Figure 3:
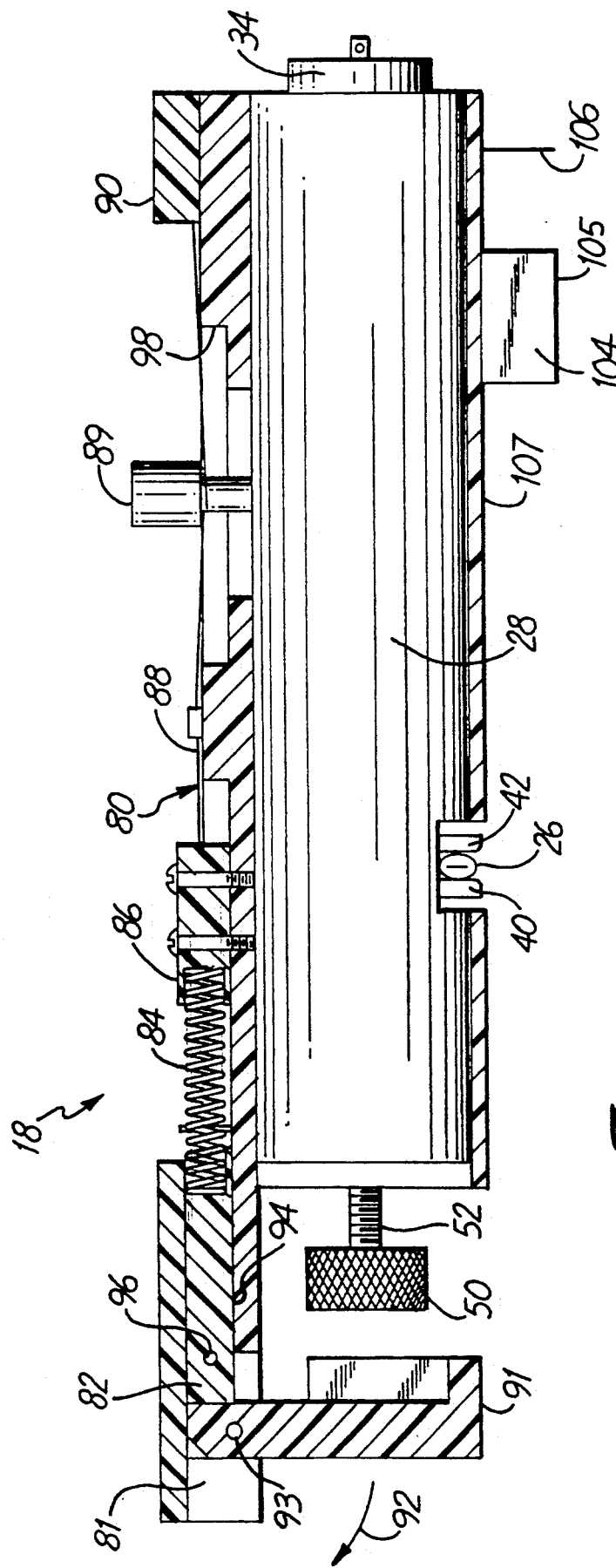
FIG. 3 shows a cable assembly used with the present invention.

The following is an illustration of one way in which the controller 14 senses that a desired flow rate has been set, and one way in which motor 34 can be locked in place relative to housing 28. FIG. 3 shows a bottom view of a portion of IV clamp 18 shown in FIG. 1. A cable assembly, shown in block form as locking mechanism 29 in FIG. 2 and shown generally at 80 in FIG. 3, includes slide 82, cable assembly spring 84, spring block 86, cable 88 and cable lock block 90. Slide 82 is slidably coupled to plate 81 in notch 94. Spring 84 abuts block 86 and slide 82. Cable 88 is attached to slide 82 through bore 96. Cable 88 is also wrapped around coupling lock 89 which is attached to motor 34. Cable 88 is also attached to cable lock block 90.

When the operator wishes to adjust the initial flow rate, or change the existing flow rate, by manipulating adjustment knob 50, the operator first pivots adjustment guard 91 along arc 92 about pivot 93. As adjustment guard 91 pivots along arc 92, it cooperates with side 82 forcing slide 82 to slide within notch 94 and compress spring 84 against spring block 86. Therefore, as slide 82 slides toward spring block 86, slack occurs in cable 88, cable 88 loosens around coupling lock 89, and coupling lock 89 is free to slide within slot 98 in plate 81 and housing 28. Since coupling lock 89 is rigidly attached to motor 34, when guard 91 is pivoted up into the adjustment position, motor 34, and clamping member 32 are free to slide within housing 28.

When the operator is through making adjustments to adjustment knob 50, the operator releases knob 50 and guard 91 automatically pivots (is urged) back down into the guarding position, under the force of spring 84. Spring 84 then urges slide 82 back into its previous position. As slide 82 moves away from spring block 86 towards its previous position, cable 88 tightens around coupling lock 89 thereby holding it in position with respect to housing 28. This allows motor 34 to effect repositioning of clamping member 32 with respect to clamping member 30.

As just described, IV clamp 18 operates in the manual mode when the operator is setting or adjusting a desired flow rate and automatically goes into the automatic mode when the operator has finished setting a new flow rate. The switching between modes is all done automatically without requiring the operator to depress any buttons or enter any data.

Figure 4:
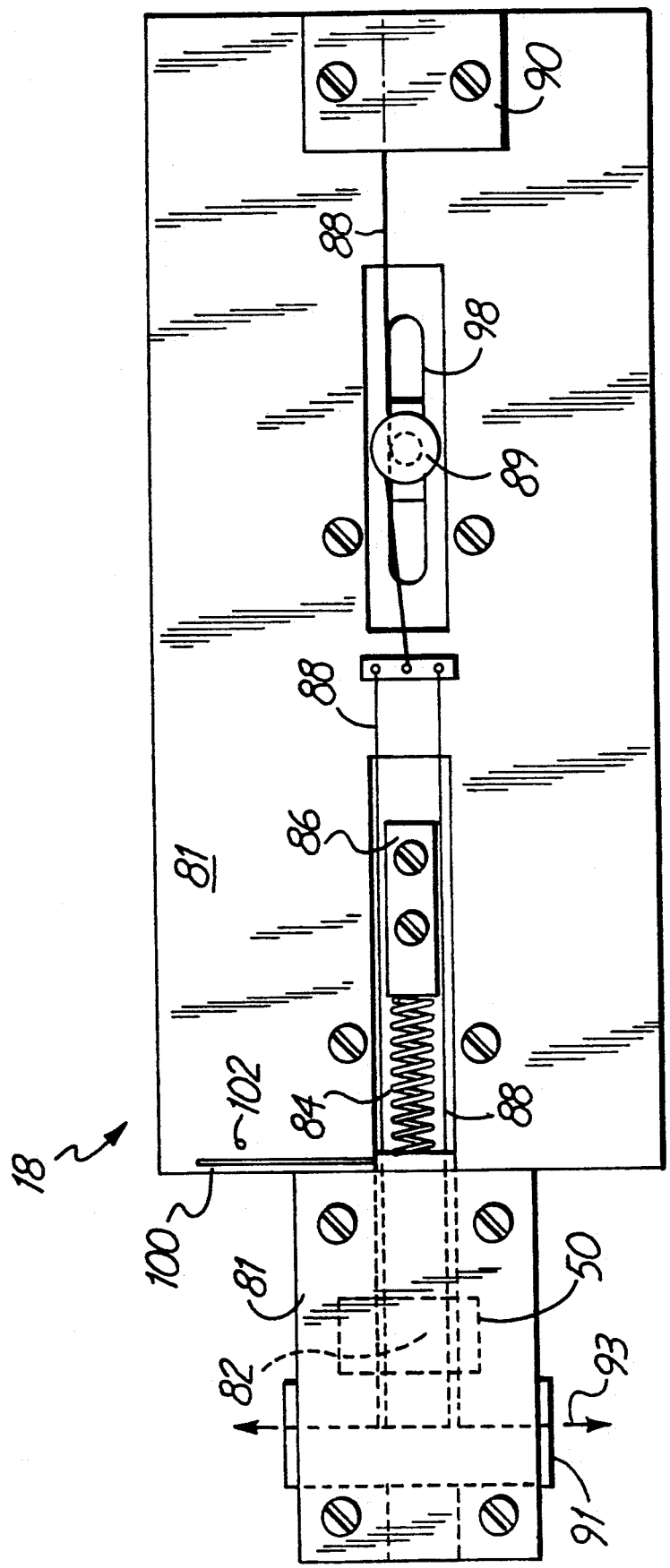
FIG. 4 shows a sensor system used with the present invention.

FIG. 4 is a side view of IV clamp 18. Adjustment knob 50 is shown in phantom. Probe 100 is attached to slide 82 and probe contact 102 is attached to plate 81 and controller 14. Also, FIG. 3 shows probe 104 coupled to a motor plate 105, and probe contact 106 coupled to either housing 28, or a cover plate 107 and controller 14.

As guard 91 is pivoted into the adjustment position, slide 82 slides towards spring block 86 and probe 100 contacts probe contact 102. Controller 14 detects the contact between probe 100 and probe contact 102 and interprets the contact as a command to enter the manual mode. In the manual mode, controller 14 stops controlling activation of motor 34 and allows the operator to manipulate adjustment knob 50 and set a desired initial flow rate or a new flow rate through IV tube 26.

To insert or remove IV tube 26, the operator adjusts knob 50 to move first and second clamping members 30 and 32 to the insertion position. This causes coupling lock 91 as well as motor plate 105 to slide along slots in housing 28. When clamping members 30 and 32 are moved to the insertion position, probe 104 makes contact with probe contact 106. Controller 14 detects the contact between probe 104 and probe contact 106 and enters an idle mode. In the idle mode, the controller can perform any desired tasks. In this preferred embodiment, the controller re-initializes clamp 18 and de-activates the flow sensor and shuts itself off to save energy.

Once the operator has inserted tube clip 38 and IV tube 26 and begins to set the initial flow rate by rotating adjustment knob 50, probe 104 breaks contact with probe contact 106. Controller 14 senses this, re-activates itself and flow rate detector 12 and displays the flow rate at display 16. However, since guard 91 is still up in the adjustment position, probe 100 is still in contact with probe contact 102. Therefore, controller 14, although no longer in the idle mode, is still in the manual mode waiting for the operator to set an initial flow rate.

Once the operator sets the initial flow rate, the guard 91 automatically pivots back down into its guarding position. This causes cable 88 to tighten around coupling lock 89 thereby holding it in place with respect to housing 28. Also, as guard 91 pivots into its guarding position, slide 82 is urged back away from slide block 86 and probe 100 breaks contact with probe contact 102. Controller 14 senses this and stores the current flow rate (i.e., the flow rate through IV tube 26 when contact between probe 100 and probe contact 102 is broken) as the desired flow rate. Controller 14 then controls activation of motor 34 based on the desired flow rate and the flow rate sensed by flow rate detector 12.

Once the desired flow rate has been manually set, controller 14 assumes a control mode. In the control mode, controller 14 controls motor 34 to adjust the position of clamping member 32 based on the desired flow rate manually set and the flow rate detected by flow rate detector 12. When controller 14 determines that the flow rate through IV tube 26 should be increased, controller 14 controls motor 34 to move clamping member 32 toward clamping member 30. This causes tube clip 38 to allow the tube reliance of IV tube 26 to open IV tube 26 wider and thereby increase the flow rate of IV fluid through IV tube 26. Conversely, when controller 14 determines that the flow rate through IV tube 26 should be decreased, controller 14 controls motor 34 to move clamping member 32 away from clamping member 30 allowing spring 44 to exert a greater pinching force on IV tube 26 through pinching members 40 and 42, thereby restricting flow of the IV fluid through IV tube 26.

It is worth noting that, once the desired flow rate has been manually set, the spring forces of springs 44 and 54 and the tube resilience of IV tube 26 are substantially in equilibrium. Thus, for motor 34 to increase or decrease the flow rate of IV fluid through IV tube 26, it is only required to overcome the incremental spring force or tube resilience necessary to open or close IV tube 26 the requisite amount. Thus, the power required for motor 34 to reposition clamping member 32 is substantially reduced over that which would be required to overcome the entire tube resilience of IV tube 26.

Similarly, it is worth noting that the desired flow rate is initially manually set. Thus, it is unnecessary for motor 34 to reposition the clamping members in order to set a desired initial flow rate. This also reduces the amount of power required by motor 34 in the operation of IV clamp 18.

In addition, the present IV clamp has a removable tube clip 38. Tube clip 38, by itself, exerts enough pinching force to completely close off IV tube 26. Thus, when removed from housing 28, tube clip 38 prevents an IV runaway condition.

Although the present invention has been described with reference to preferred embodiments, workers skilled in the art will recognize that changes may be made in form and detail without departing from the spirit and scope of the invention.

What is claimed is:

1. An apparatus for clamping an intravenous (IV) tube, having a tube resilience, in an infusion device to control flow rate of IV fluid in the IV tube, the apparatus comprising:
   a tube clip having first and second pinching members and first biasing means for exerting a pinching force on the tube clip to bias the first and second pinching members toward one another, the first and second pinching members being positionable for insertion of the IV tube between the first and second pinching members, the first and second pinching members each having a first and second end and wherein the first and second pinching members are pivotally connected at a point between the first and second ends;
   a clamp housing;
   a pair of clamping members coupled to the clamp housing, the clamping members positionable for insertion of a portion of the tube clip between the pair of clamping members, the pair of clamping members operably engaging the tube clip to variably offset the pinching force based on relative position of the pair of clamping members with respect to one another; and
   manual adjustment means, coupled to at least one of the pair of clamping members, for manually adjusting the relative position of said one of the pair of clamping members relative to the other of the pair of clamping members to set a desired flow rate in the IV tube.

2. The apparatus of claim and further comprising:

second bias means, coupled to at least one of the pair of clamping members, for variably exerting a spring force on the tube clip through said one of the pair of clamping members based on manual adjustment of the pair of clamping members, and wherein the pinching force, the tube resilience and the spring force are substantially in equilibrium when the desired flow rate is manually set.

3. The apparatus of claim 2 and further comprising:
a clamp motor, coupled to at least one of the pair of clamping members, for repositioning said one of the pair of clamping members to adjust the relative position of the pair of clamping members with respect to one another.

4. The apparatus of claim 3 and further comprising:
a flow rate detector for detecting the flow rate of the IV fluid through the IV tube; and
a controller, coupled to the flow rate detector and the clamp motor, for controlling the clamp motor based on the desired flow rate and the flow rate detected.

5. The apparatus of claim 4 wherein the first biasing means comprises:
a spring coupled to the first and second pinching members.

6. The apparatus of claim 5 wherein the second bias means comprises:
a spring operably coupled to the clamp housing and coupled to said one of the pair of clamping members.

7. The apparatus of claim 6 wherein the spring coupled to the first and second pinching members has a spring force sufficient to cause the first and second pinching members to pinch the IV tube completely closed.

8. The apparatus of claim 2 wherein the manual adjustment means and the second bias means are coupled to opposite ones of the pair of clamping members.

9. The apparatus of claim 1 wherein the first biasing means is coupled to the first ends of the first and second pinching members and wherein the second ends of the pinching members are positionable for insertion of the IV tube between the second ends of the first and second pinching members.

10. The apparatus of claim 1 wherein the second ends of the first and second pinching members are inserted between, and operably engage the pair of clamping members.

11. An apparatus for clamping an intravenous tube, having a tube resilience, in an infusion device to control flow rate of IV fluid in the IV tube, the apparatus comprising:
a tube clip having first and second pinching members and first biasing means for exerting a pinching force on the tube clip to bias the first and second pinching members toward one another, the first and second pinching members being positionable for insertion of the IV tube between the first and second pinching members, the first and second pinching members each having a first and second end and wherein the first and second pinching members are pivotally connected at a point between the first and second ends;
a clamp housing;
a pair of clamping members coupled to the clamp housing, the clamping members positionable for insertion of a portion of the tube clip between the pair of clamping members, the pair of clamping members operably engaging the tube clip to variably offset the pinching force based on relative position of the pair of clamping members with respect to one another; and
a clamp motor, coupled to at least one of the pair of clamping members, for repositioning said one of the pair of clamping members to adjust the relative position of the pair of clamping members with respect to one another.

12. The apparatus of claim 11 and further comprising:
a flow rate detector for detecting the flow rate of the IV fluid through the IV tube; and
a controller, coupled to the flow rate detector and the clamp motor, for controlling the clamp motor based on a desired flow rate and the flow rate detected.

13. The apparatus of claim 12 and further comprising:
manual adjustment means, coupled to at least one of the pair of clamping members, for manually adjusting a relative position of said one of the pair of clamping members relative to the other of the pair of clamping members to set the desired flow rate in the IV tube.

14. The apparatus of claim 13 and further comprising:
second bias means, coupled to at least one of the pair of clamping members, for variably exerting a spring force on the tube clip through said one of the pair of clamping members based on manual adjustment of the pair of clamping members, and wherein the pinching force, the tube resilience and the spring force are substantially an equilibrium when the desired flow rate is manually set.

15. The apparatus of claim 14 wherein the first biasing means has a spring force sufficient to cause the first and second pinching members to pinch the IV tube completely closed.

16. The apparatus of claim 11 wherein the first biasing means is coupled to the first ends of the first and second pinching members and wherein the second ends of the pinching members are positionable for insertion of the IV tube between the second ends of the first and second pinching members.

17. The apparatus of the claim 16 wherein the second ends of the first and second pinching members are inserted between, and operably engage the pair of clamping members.

* * * * *